US007393325B2

(12) United States Patent
Barthe et al.

(10) Patent No.: US 7,393,325 B2
(45) Date of Patent: Jul. 1, 2008

(54) METHOD AND SYSTEM FOR ULTRASOUND TREATMENT WITH A MULTI-DIRECTIONAL TRANSDUCER

(75) Inventors: Peter G. Barthe, Phoenix, AZ (US); Michael H. Slayton, Tempe, AZ (US)

(73) Assignee: Guided Therapy Systems, L.L.C., Mesa, AZ (US)

( * ) Notice: Subject to any disclaimer, the term of this patent is extended or adjusted under 35 U.S.C. 154(b) by 0 days.

(21) Appl. No.: 10/944,499

(22) Filed: Sep. 16, 2004

(65) Prior Publication Data

US 2006/0058707 A1    Mar. 16, 2006

(51) Int. Cl.
*A61B 8/00* (2006.01)

(52) U.S. Cl. .................. 600/439; 600/437; 600/444; 600/459; 601/2

(58) Field of Classification Search .......... 600/437, 600/439, 466, 444, 459; 601/1–5; 604/20–22
See application file for complete search history.

(56) References Cited

U.S. PATENT DOCUMENTS

| | | | | |
|---|---|---|---|---|
| 3,913,386 | A | * | 10/1975 | Saglio ................... 73/644 |
| 4,101,795 | A | * | 7/1978 | Fukumoto et al. ........ 310/336 |
| 4,381,007 | A | | 4/1983 | Doss |
| 4,528,979 | A | | 7/1985 | Marchenko et al. |
| 4,858,613 | A | | 8/1989 | Fry |
| 4,875,487 | A | | 10/1989 | Seppi |
| 4,917,096 | A | | 4/1990 | Englehart et al. |
| 4,951,653 | A | | 8/1990 | Fry |
| 4,955,365 | A | | 9/1990 | Fry |
| 5,036,855 | A | | 8/1991 | Fry |
| 5,054,470 | A | | 10/1991 | Fry |
| 5,117,832 | A | | 6/1992 | Sanghvi |
| 5,163,421 | A | | 11/1992 | Bernstein |
| 5,230,334 | A | | 7/1993 | Klopotek |
| 5,269,297 | A | | 12/1993 | Weng |

(Continued)

FOREIGN PATENT DOCUMENTS

WO        WO9832379        3/1998

(Continued)

OTHER PUBLICATIONS

International Search Report and Written Opinion from corresponding PCT Patent Application No. PCT/US2005/033046.

*Primary Examiner*—Brian L. Casler
*Assistant Examiner*—Baisakhi Roy
(74) *Attorney, Agent, or Firm*—Snell & Wilmer L.L.P.

(57) ABSTRACT

A method and system for ultrasound treatment utilizing a multi-directional transducer to facilitate treatment, such as therapy and/or imaging or other tissue parameter monitoring, in two or more directions. In accordance with an exemplary embodiment, a multi-directional transducer comprises a transduction element configured to provide for ultrasound energy, such as radiation, acoustical energy, heat energy, imaging, positional information and/or tissue parameter monitoring signals in two or more directions. The transduction element can comprise various materials for providing ultrasound energy or radiation, such as piezoelectric materials, with and without matching layers. In addition, the transduction element can be configured for substantially uniform, focused and/or defocused radiation patterns, as well as for single, multiple-element and/or multiple-element array configurations. In addition, an exemplary multi-directional transducer can comprise multiple elements, either side by side, stacked or in an array.

45 Claims, 7 Drawing Sheets

U.S. PATENT DOCUMENTS

| | | | |
|---|---|---|---|
| 5,492,126 A | 2/1996 | Hennige | |
| 5,496,256 A * | 3/1996 | Bock et al. | 601/2 |
| 5,526,815 A | 6/1996 | Granz | |
| 5,601,526 A | 2/1997 | Chapelon | |
| 5,690,608 A | 11/1997 | Watanabe | |
| 5,755,753 A | 5/1998 | Knowlton | |
| 5,762,066 A * | 6/1998 | Law et al. | 600/439 |
| 5,873,902 A | 2/1999 | Sanghvi | |
| 5,919,219 A | 7/1999 | Knowlton | |
| 5,931,805 A | 8/1999 | Brisken | |
| 5,984,882 A | 11/1999 | Rosenschein | |
| 6,050,943 A | 4/2000 | Slayton et al. | |
| 6,071,239 A | 6/2000 | Cribbs | |
| 6,093,883 A | 7/2000 | Sanghvi | |
| 6,113,558 A | 9/2000 | Rosenschein | |
| 6,113,559 A | 9/2000 | Klopotek | |
| 6,135,971 A | 10/2000 | Hutchinson | |
| 6,241,753 B1 | 6/2001 | Knowlton | |
| 6,296,619 B1 * | 10/2001 | Brisken et al. | 604/22 |
| 6,311,090 B1 | 10/2001 | Knowlton | |
| 6,325,769 B1 | 12/2001 | Klopotek | |
| 6,361,531 B1 | 3/2002 | Hissong | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,405,090 B1 | 6/2002 | Knowlton | |
| 6,409,720 B1 | 6/2002 | Hissong | |
| 6,413,254 B1 | 7/2002 | Hissong | |
| 6,428,532 B1 | 8/2002 | Doukas | |
| 6,430,446 B1 | 8/2002 | Knowlton | |
| 6,432,101 B1 | 8/2002 | Weber | |
| 6,436,061 B1 | 8/2002 | Costantino | |
| 6,453,202 B1 | 9/2002 | Knowlton | |
| 6,461,378 B1 | 10/2002 | Knowlton | |
| 6,470,216 B1 | 10/2002 | Knowlton | |
| 6,500,141 B1 | 12/2002 | Irion | |
| 6,595,934 B1 | 7/2003 | Hissong | |
| 6,607,498 B2 | 8/2003 | Eshel | |
| 6,626,854 B2 | 9/2003 | Friedman | |
| 6,626,855 B1 | 9/2003 | Weng | |
| 6,645,162 B2 | 11/2003 | Friedman | |
| 6,685,640 B1 | 2/2004 | Fry | |
| 6,692,450 B1 | 2/2004 | Coleman | |
| 6,699,237 B2 | 3/2004 | Weber | |
| 6,719,694 B2 | 4/2004 | Weng | |
| 6,974,417 B2 * | 12/2005 | Lockwood et al. | 600/459 |
| 7,063,666 B2 | 6/2006 | Weng | |
| 7,094,252 B2 | 8/2006 | Koop | |
| 7,258,674 B2 | 8/2007 | Cribbs et al. | |
| 2001/0041880 A1 | 11/2001 | Brisken et al. | |
| 2002/0040199 A1 | 4/2002 | Klopotek | |
| 2002/0082528 A1 | 6/2002 | Friedman | |
| 2002/0082589 A1 | 6/2002 | Friedman | |
| 2002/0128648 A1 | 9/2002 | Weber | |
| 2003/0032900 A1 | 2/2003 | Ella | |
| 2003/0040739 A1 | 2/2003 | Koop | |
| 2003/0083536 A1 | 5/2003 | Eshel | |
| 2003/0191396 A1 | 10/2003 | Sanghvi | |
| 2003/0212351 A1 | 11/2003 | Hissong | |
| 2004/0015106 A1 | 1/2004 | Coleman | |
| 2004/0039312 A1 | 2/2004 | Hillstead | |
| 2004/0059266 A1 | 3/2004 | Fry | |
| 2004/0210214 A1 | 10/2004 | Knowlton | |
| 2005/0055073 A1 | 3/2005 | Weber | |
| 2005/0154314 A1 | 7/2005 | Quistgaard | |
| 2005/0187495 A1 | 8/2005 | Quistgaard | |
| 2005/0261584 A1 | 11/2005 | Eshel | |
| 2005/0267454 A1 | 12/2005 | Hissong | |
| 2006/0089688 A1 | 4/2006 | Panescu | |
| 2006/0122509 A1 | 6/2006 | Desilets | |
| 2006/0241440 A1 | 10/2006 | Eshel | |
| 2007/0035201 A1 | 2/2007 | Desilets | |
| 2007/0055156 A1 | 3/2007 | Desilets | |

FOREIGN PATENT DOCUMENTS

| | | |
|---|---|---|
| WO | WO9949788 | 7/1999 |
| WO | WO0128623 | 4/2001 |
| WO | WO0182777 | 8/2001 |
| WO | WO0182778 | 11/2001 |
| WO | WO0187161 | 11/2001 |
| WO | WO0224050 | 3/2002 |
| WO | WO03070105 | 8/2003 |

* cited by examiner

METHOD AND SYSTEM FOR ULTRASOUND TREATMENT WITH A MULTI-DIRECTIONAL TRANSDUCER

FIELD OF INVENTION

This invention generally relates to an ultrasound system, and more particularly, to a method and system for ultrasound treatment utilizing a multi-directional transducer.

BACKGROUND OF THE INVENTION

Ultrasound therapy is a powerful technique that uses acoustic energy to provide medical treatment. Ultrasound therapy typically uses an ultrasound transducer or probe to radiate the acoustic energy to a treatment region. Various design parameters of the transducer impact the attainable level of control. For example, the amplitude, temporal control and spatial harnessing of the acoustic energy can be varied depending upon the treatment desired. In addition, the acoustic power output capability, the allowable frequency range of operation, and the size and shape of the power output of the transducer can be varied to provide a desired acoustic radiation pattern.

An ultrasound transducer typically includes a transduction element having a piezoelectrically active layer, such as lead zirconante titanate (PZT). The piezoelectrically active layer receives electrical drive signals that cause the piezoelectrically active layer to expand and contract, and thus convert the electrical drive signals to mechanical waves. These mechanical waves are ultimately acoustically coupled to a tissue region. The piezoelectric layer is typically hard compared to the tissue, which entails the use of acoustic matching layers and backing materials to dampen any high-Q resonances and extend the useful bandwidth of operation for the transducer.

To achieve ultrasound ablation or collagen reformation effects in tissue, a relatively high power output is required as compared to the ultrasound acoustic power levels needed for diagnostic applications. Many backing materials such as rubber that are configured within ultrasound transducers tend to absorb a large amount of the power, thus resulting in heating of the backing material as well as an active transduction layer. This heating of the backing material can cause the transducer to overheat and destruct, and cause the transducer to have a low efficiency and a reduced power output. One alternative to backing materials has been to configure the transducers as unloaded or "air-backed." However, such air-backed transducers have reduced bandwidths.

Figure 1:
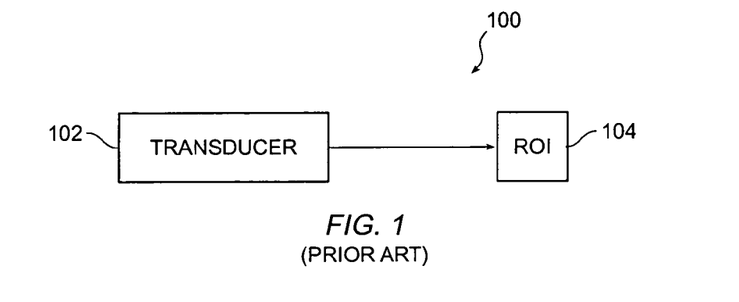
FIG. 1 illustrates a block diagram of a prior art ultrasound therapy system.

Moreover, conventional transducers are configured for providing radiation in only a single-direction. For example, with reference to a block diagram of an ultrasound system 100 illustrated in FIG. 1, a conventional transducer 102 is configured to provide therapy only to a single region of interest 104, i.e., configured to provide acoustic energy in only one direction. Conventional transducers are limited to single direction radiation whether having backing materials or being air-backed.

Figure 2:
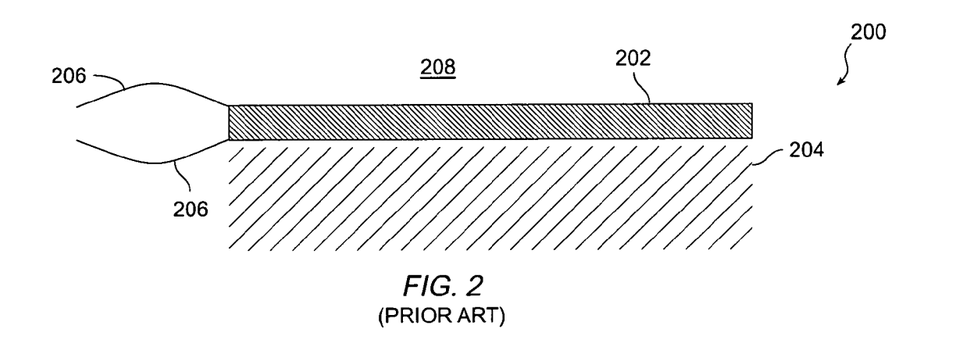
FIG. 2 illustrates a diagram of a prior art ultrasound therapy transducer.

For example, with reference to FIG. 2, a conventional transducer 200 comprises a transduction element 202 configured as an air-backed transducer, i.e., having an air-backing 208, and having electrical leads 206. Air-backing 208 is configured with transduction element 202 on one side, thus allowing transducer 200 to only transmit energy in a single radiation pattern 204 on a side opposite that of air-backing 208. Conventional backing materials also limit such transducers 200 to single-direction radiation, with the backing material configured on a first side, and transducer 200 generating radiation from a second side towards a single treatment region. To address other treatment regions, transducer 200 requires significant rotational or translational movements to provide such treatment, thus requiring a significant amount of time and power.

SUMMARY OF THE INVENTION

In accordance with various aspects of the present invention, a method and system for ultrasound treatment utilizing a multi-directional transducer to facilitate treatment in two or more directions are provided. In accordance with an exemplary embodiment, a method and system for multi-directional ultrasound treatment may comprise a control system and a multi-directional transducer. The control system may comprise any type of conventional control system with various components such as a processor, a display, and/or an input/output device. The control system may be coupled to the multi-directional transducer in various manners.

An exemplary multi-directional transducer is configured to facilitate treatment, such as therapy and/or imaging or other tissue parameter monitoring, in two or more directions. In accordance with an exemplary embodiment, a multi-directional transducer comprises a transduction element configured to provide for ultrasound energy, such as radiation, acoustical energy, heat energy, imaging, positional information and/or tissue parameter monitoring signals in two or more directions. The transduction element can comprise various materials for providing ultrasound energy or radiation, such as piezoelectric materials, with and without matching layers. In addition, the transduction element can be configured for substantially uniform, focused and/or defocused radiation patterns, as well as for single, multiple-element and/or multiple-element array configurations. In addition, an exemplary multi-directional transducer can comprise multiple elements, either side by side, stacked or in an array. Accordingly, an exemplary multi-directional transducer can provide multi-directional capabilities from a single transduction element, e.g., a single PZT crystal, or multiple elements, with the ability for further configuring the shape and/or orientation of the transduction elements to provide a variety of functions, such as therapy and/or various tissue parameter monitoring functions.

In accordance with other aspects of the present invention, an exemplary method and system for ultrasound treatment utilizing a multi-directional transducer may be used for therapy and/or imaging applications in two or more directions. In addition, the multi-directional transducer may be rotated and/or translated to provide for treatment, such as therapy and/or imaging, over a large region. Since the multi-directional transducer can treat multiple regions at the same time, the amount of rotational and/or translational movement needed for treatment can be minimized. As a result, the overall treatment time and power output requirements can be reduced.

BRIEF DESCRIPTION OF THE DRAWINGS

The subject matter of the invention is particularly pointed out and distinctly claimed in the concluding portion of the specification. The invention, however, both as to organization and method of operation, may best be understood by reference to the following description taken in conjunction with the claims and the accompanying drawing figures, in which like parts may be referred to by like numerals:

DETAILED DESCRIPTION

The present invention may be described herein in terms of various components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical or treatment contexts and that the exemplary embodiments relating to an ultrasound multi-directional transducer as described herein are merely a few of the exemplary applications for the invention. For example, the principles, features and methods discussed may be applied to any medical or other tissue or treatment application.

A method and system for ultrasound treatment utilizing a multi-directional transducer to facilitate treatment in two or more directions are provided. With reference to an exemplary embodiment illustrated in FIG. 3, an exemplary system 300 for multi-directional ultrasound treatment includes a control system 302 and a multi-directional transducer 304. Control system 302 may be coupled to multi-directional transducer 304 in various manners to provide control of multi-directional transducer 304, including the transmission and reception of signals to analyze and/or display information.

Figure 3:
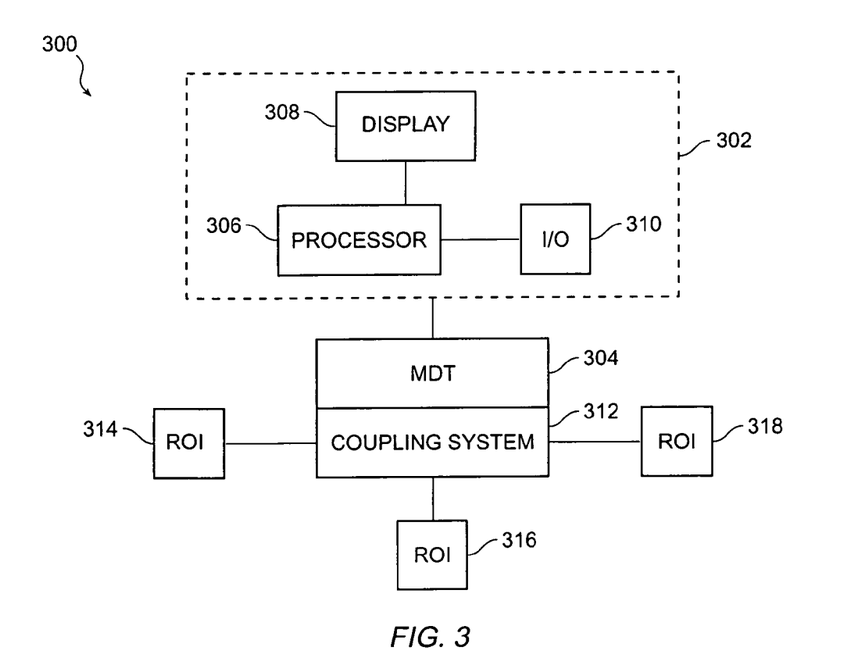
FIG. 3 illustrates a block diagram of an exemplary embodiment of a system for ultrasound treatment in accordance with the present invention.

Control system 302 may comprise a processor 306, a display 308 and/or an input/output device 310. Processor 306 may comprise a personal computer, a Unix system, or any other conventional processing unit. Display 308 may comprise a monitor, a LCD screen, or any other device configured to display an image. Input/output device 310 may comprise a keyboard, a mouse, a touch-screen, e.g., a touch-screen within display 308, or any other device for inputting and outputting information. The information from input/output device 310 may be received or transmitted in any form, such as manually, by analog device, by digital device, and/or by any other mechanisms. Processor 306, display 308 and input/output device 310 may be coupled together in any manner. By coupling, processor 306, display 308 and input/output device 310 may be directly connected to each other; or processor 306, display 308 and input/output device 310 can be connected through one or more various elements, wherein a signal travels to/from one component to another. The various coupling elements for processor 306, display 308 and input/output device 310 can include but are not limited to the internet, a wireless network, a conventional wire cable, an optical cable or connection through air, water, or any other medium that conducts signals, and any other coupling device or medium.

As further exemplified in FIG. 3, multi-directional transducer 304 may facilitate treatment with two or more regions of interest (ROI) such as ROI 314, ROI 316, and/or ROI 318. During treatment, multi-directional transducer 304 may simultaneously transmit to or receive from ROI 314, ROI 316, and/or ROI 318 any signal configuration, such as, for example, information, energy, sound waves, and heat waves. While three ROIs are illustrated in FIG. 3, multi-directional transducer 304 may facilitate treatment with one, two, four, or more ROIs. ROIs 314, 316 and 318 may comprise any region of interest within a patient, such as a superficial region, subcutaneous region and/or a deep treatment region.

To facilitate coupling of multi-directional transducer 304 to region(s) of interest 314, 316 and/or 318, multi-directional transducer 304 can further comprise a coupling system 312 configured for acoustic coupling of ultrasound energy and signals. Coupling system 312 may facilitate such coupling through use of various coupling mediums, including air and other gases, water and other fluids, gels, solids, and/or any combination thereof, or any other medium that allows for signals to be transmitted between multi-directional transducer 304 and region(s) of interest 314, 316 and/or 318. In addition to providing a coupling function, in accordance with an exemplary embodiment, coupling system 312 can also be configured for providing temperature control during the treatment application. For example, coupling system 312 can be configured for controlled cooling of an interface surface or region between multi-directional transducer 304 and region of interest 210 by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial and/or thermal energy control of multi-directional ultrasound treatment system 300.

Exemplary multi-directional transducer 304 can be configured in various manners. For example, with reference to FIG. 4A, a multi-directional transducer probe 400 comprises a transduction element 402 coupled to electric leads 404. Transduction element 402 may comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. Transduction element 402 may also comprise one or more matching layers configured along with the piezoelectrically active material. In addition to or instead of piezoelectrically active material, transduction element 402 can comprise any other materials configured for generating radiation and/or acoustical energy.

Electrical leads 404 are configured to enable power to be transmitted to and signals received from transduction element 402, and can comprise any wiring type, configuration and arrangement for use with ultrasound transducers. Transduction element 402 may also be coupled to electrical leads 404 in various manners. For example, with reference to an exemplary embodiment illustrated in FIG. 4A, transduction element 402 may be coupled with electrical leads 404 on only one end; however, electrical leads 404 may also be coupled together on an opposite end, or any other location along transduction element 402.

Figure 4A:
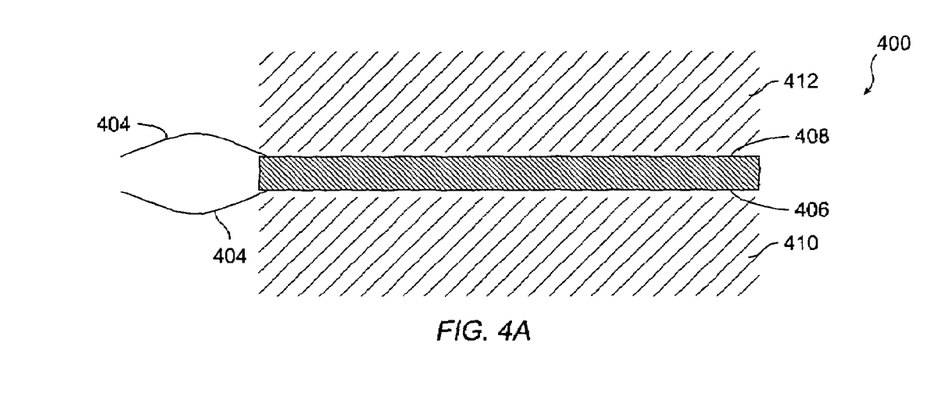
FIGS. 4A and 4B illustrate an exemplary embodiment of a multi-directional transducer probe in accordance with the present invention.
Figure 4B:
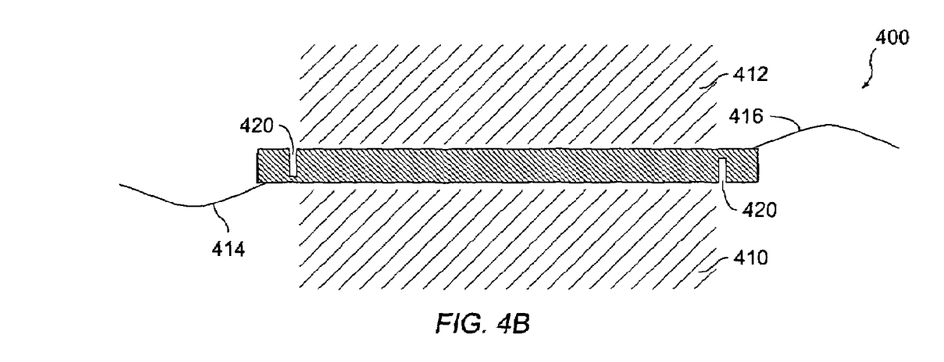

With reference to another embodiment illustrated in FIG. 4B, transduction element 402 may be configured with a first electrical lead 412 attached a first end and a second electrical lead 414 attached to an opposing, second end of transduction element 402. While FIG. 4B illustrates electrical lead 412 coupled to one end of transduction element 402 and electrical lead 414 coupled to the opposite end of transduction element 402, electrical lead 412 and electrical lead 414 may be coupled to any location between either end of transduction element 402. Coupling of the electronic leads is not limited to the embodiments depicted in either FIG. 4A or 4B, and may comprise any electrical coupling configuration for providing power to and receiving signals from transduction element 402.

Transduction element 402 may also be configured with various mounting mechanisms. For example with reference to FIG. 4B, transduction element 402 may be configured with mechanical notches 420 configured for mounting of transduction element 402 within transducer 400. Mechanical notches 420 can be configured to reduce interference with the electrical coupling. While mechanical notches 420 may be configured proximate to opposite ends of transduction element 402, mechanical notches 420 may also be configured along any location of transduction element 402. Mounting mechanisms for use with transduction element 402 are not limited to the embodiments depicted in either FIG. 4A or 4B, and may comprise any other mounting mechanisms for reduction of electrical coupling and/or improvement of communications with a transducer.

Multi-directional transducer probe 400 can be configured to transmit signals in two or more directions. These signals can include for example acoustic energy, heat energy, imaging information, positional information and/or tissue parameter monitoring. Multi-directional transducer probe 400 can transmit signals in two or more directions by exposing two or more radiating surface areas, i.e., faces, of transduction element 402 to tissue or other ROIs. For example, transduction element 402 may transmit signals from both a first front firing face 406 and a second rear firing face 408 to a region of interest, e.g., by providing two or more radiation patterns, such as a front face radiation pattern 410 and a rear face radiation pattern 412.

Rear firing face 408 is configured to provide some damping effects to acoustical energy provided by front firing face 406 through acoustical loading at rear firing face 408, thus enabling increased bandwidth for multi-directional transducer 400. For example, a large acoustic impedance mismatch often exists between a transduction material, such as PZT and a load, such as tissue. When the transduction material is electrically excited, and if the transduction material is lightly loaded or undamped, it will tend to preferentially vibrate at a single frequency or a narrow frequency range, e.g., one analogous to the ringing of a bell. In addition, loading creates a short impulse response in the time domain, resulting in a wideband frequency response. However, since multi-directional transducer probe 400 can be suitably loaded on both faces 406 and 408, the additional loading increases the effective range of frequencies over which transducer probe 400 can operate. Further, increasing the transmission bandwidth can facilitate changing of the transmit frequency, thus enabling significant control of any tissue heating and treatment effects.

In addition, since rear firing face 408 does not need acoustic isolation to suitably operate, a more compact transducer design can result. Moreover, with both faces 406 and 408 being configured to allow for a coupling fluid, such as water, to flow over the radiating surface areas, greater cooling can be realized for transduction element 402. Improved cooling properties can allow for higher electro-acoustic efficiency to be maintained, thus yielding for example an increased output capability as well as an improved reliability and lifetime.

While FIG. 4A depicts both front firing face 406 and rear firing face 408 as being substantially opposed, e.g., front and rear, faces 406 and 408 may be configured to be adjacent to one another, or anywhere in between. Further, while FIG. 4A depicts multi-directional transducer probe 400 transmitting signals in two directions, multi-directional transducer probe 400 may be configured to transmit signals from three, four, or more firing faces, configured in various orientations around transducer element 402. According, with two or more radiating surface areas, and with improved electro-acoustic loading, an increase in acoustic power can be suitably realized.

Multi-directional transducer 400 can be configured for transmitting and/or receiving signals in two or more directions simultaneously. However, with a reduced possibility for overheating or overcooling with radiating faces 406 and 408, two radiating zones or regions of interest may be treated by transducer 400 with only minimal thermal cross-talk. In addition to simultaneous radiating or firing, faces 406 and 408 can be configured for transmitting and/or receiving signals in an alternating manner or for other timing intervals. For example, firing faces 406 and 408 can be configured to generate radiation or other signals at the same time, or in an alternating or other non-simultaneous fashion. In addition, one or more other faces can be configured to fire as the same time as faces 406 and 408, or at different times than faces 406 and 408.

Due to at least two radiating surface areas for transduction element 402, such as faces 406 and 408, and improved electro-acoustic loading, an increase in acoustic power can be realized. Moreover, with multi-directional transducer 400 requires less treatment time than conventional single-directional transducers to deliver a given amount of radiation/energy. Further, with the ability to provide simultaneous radiating from two or more faces, i.e., two or more radiating surface areas, without overheating, overcooling and generating extensive thermal crosstalk, the planning of treatment applications can be readily predicted and managed.

An exemplary multi-directional transducer can provide multi-directional capabilities from a single transduction element, e.g., a PZT crystal, with the ability for further configuring the shape and/or orientation of the transduction element to provide a variety of functions, such as therapy and/or various tissue parameter monitoring functions. For example, due to the multi-directional capabilities of transduction element 402, multi-directional transducer probe 400 can suitably allow for therapy and/or imaging applications, or any other applications such as temperature measurement, in two or more directions. For example, multi-directional probe 400 can allow for therapy treatment to be provided to or imaging information captured from to two or more ROIs from both faces 406 and 408, or therapy treatment being facilitated from one of faces 406 and 408 and imaging information being facilitated from the other. Multi-directional transducer probe 400 can also allow for therapy and/or imaging to occur simultaneously or at different timing intervals.

Multi-directional transducer probe 400 may be configured in various manners to provide for interstitial or percutaneous treatment of ROIs. For example, multi-directional transducer probe 400 can be configured external to the outer tissue of a patient for percutaneous-type treatment of two or more ROIs. In addition, multi-directional transducer probe 400 can be coupled to the outer tissue of the patient through various types of coupling mediums, such as gels, water or other coupling substances or materials.

Multi-directional transducer probe 400 can also be configured for interstitial and/or other invasive applications wherein multi-directional transducer probe 400 is positioned within the patient. To facilitate such interstitial and/or other invasive applications, multi-directional transducer probe 400 can also be configured within a tubular member. For example, with momentary reference to FIG. 5, an exemplary multi-directional transducer probe 500 can comprise a transduction element 502 configured within a tubular member 504. Tubular member 504 is configured to provide a covering and/or shield between transduction element 502 and tissue regions of the patient. Tubular member 504 can comprise various types of materials and composites, now known or hereinafter devised, for covering transduction element 502. In addition, transducer 500 can be configured with or without acoustic matching within tubular member 504. However, tubular member 504 is not required for use with transduction element 502, and a multi-directional transducer can include any other member, component, matching layer or other material for facilitating invasive operation of an interstitial probe configuration within a patient.

In accordance with another aspect of the present invention, an exemplary multi-directional transducer probe may be configured for rotational and/or translational operation to provide treatment, such as therapy and/or imaging, over a larger ROI. Since an exemplary multi-directional transducer can treat multiple ROIs, even simultaneously, the amount of rotational and/or translational movement needed for treatment can be minimized. As a result, the overall treatment time and power output requirements are reduced.

For example, with reference again to FIG. 5, a multi-directional transducer 500 comprising transduction element 502 can be configured within tubular member 504. Multi-directional transducer probe 500 may be suitably rotated, in a clockwise and/or counterclockwise manner, to allow for a firing face to be configured to provide radiation to different treatment areas. For example, a first face 504 and a second face 506 can initially be configured to provide radiation to treatment areas 510 and 512, respectively. Faces 504 and 506 can be configured during rotational movement to provide radiation to different treatment areas.

For example, with reference again to FIG. 5, a multi-directional transducer 500 comprising transduction element 502 can be configured within tubular member 504. Multi-directional transducer probe 5(10 may be suitably rotated, in a clockwise and/or counterclockwise manner, to allow for a firing ace to be configured to provide a radiation to different treatment areas. For example, a first face 508 and a second face 506 can initially be configured to provide radiation to treatment areas 510 and 512, respectively. Faces 508 and 506 can be configured during rotational movement to provide radiation to different treatment areas.

Figure 5:
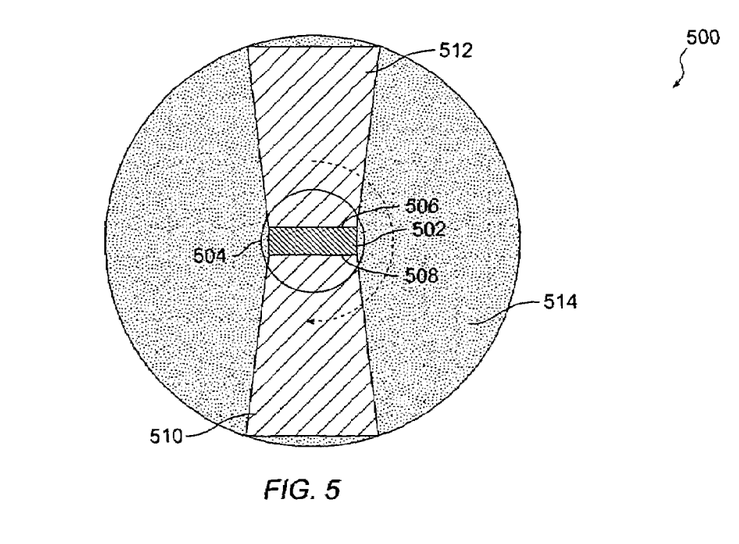
FIG. 5 illustrates an exemplary embodiment of a method for treatment in accordance with the present invention.

For example, upon a rotational movement of approximately 180 degrees, faces 508 and 506 can be configured to provide radiation to originally opposing treatment areas 512 and 510, respectively. Moreover, if during rotation transduction element 502 substantially provides radiation on a continuing basis from faces 508 and 506, multi-directional transducer can suitably insonify a large volume of tissue in approximately one-half the time or less of conventional transducers. thus while conventional single-directional probes require an approximate 360-degree rotational movement before insonifying a full volume of treatment area, multi-directional transducer probe 500 may be rotated for approximately 180-degrees or less to allow for treatment of an entire ROI 514. In other words, a rotation of zero to 190-degrees of transducer probe 500 can facilitate treatment of a 360-degree sector. Such rotational movement by multi-directional transducer probe 500 can be realized in a clockwise and/or counterclockwise manner. As a result, the overall treatment time and power output requirements for a treatment region are reduced.

While FIG. 5 illustrates a rotational multi-directional probe 500 using a transduction element 502 that can transmits signals from two faces, a rotational interstitial probe may also be configured to transmit signals from more than two faces. For example with reference to FIGS. 6A and 6B, a rotational interstitial probe 600 comprises a multi-directional transduction element 602 configured within a tube 604 and having four faces 610, 612, 614, and/or 616. Faces 610, 612, 614, and/or 616 may be air-backed to provide treatment, such as imaging and/or therapy. FIG. 6B illustrates transducer probe 600 after approximately 90-degrees of rotation such that an entire ROI 612 may be treated. Thus, increasing the number of radiating surface areas can enable treatment over a larger ROI with less rotational movement. Accordingly, additional faces of transduction element 602 can facilitate treatment over a given ROI in less treatment time and output power.

Multi-directional transducer probe 500 may also be translated in any direction to insonify a large volume of tissue. For example, by translating transducer probe 506 in a sideways direction, even more tissue may be treated. In addition, multi-directional transducer 500 may also be configured for rotational and translational movement at the same time, or in an alternating or interchanging manner. Accordingly, multi-directional transducer 500 can be suitably rotated and/or translated in any manner to provide treatment to a larger ROI.

Figure 6A:
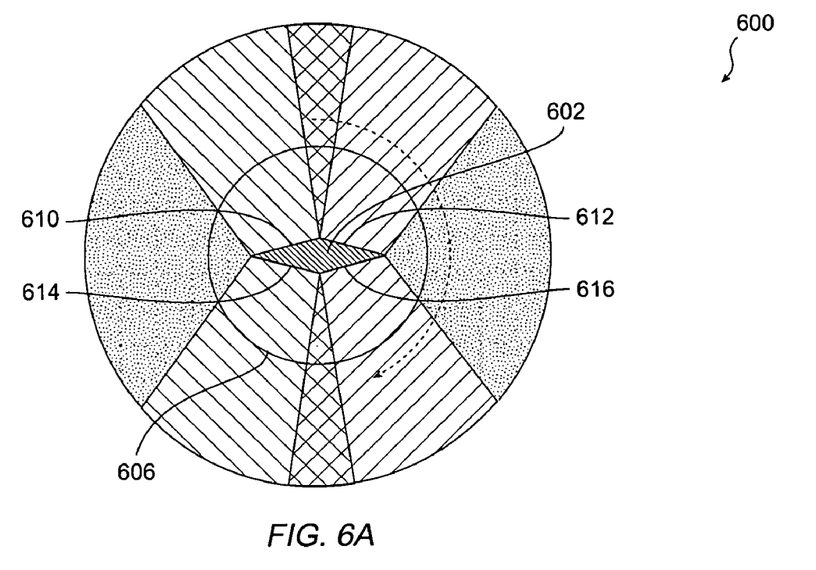
FIG. 6 illustrates another exemplary embodiment of a method for treatment in operation in accordance with the present invention.
Figure 6B:
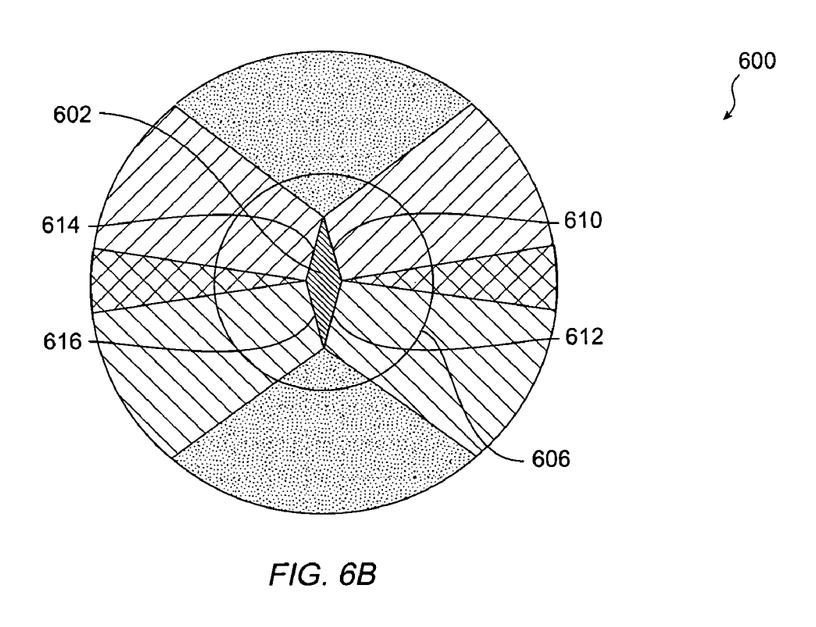
Figure 7A:
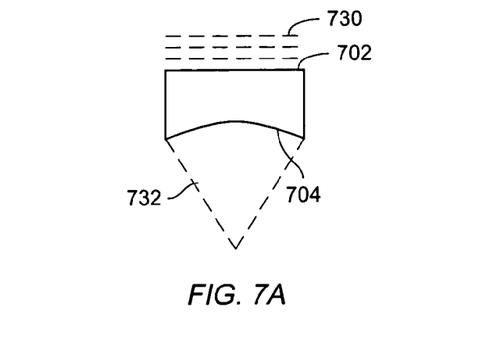
FIGS. 7A-7E illustrate exemplary embodiments of surface curvatures for a transducer in accordance with the present invention.
Figure 7B:
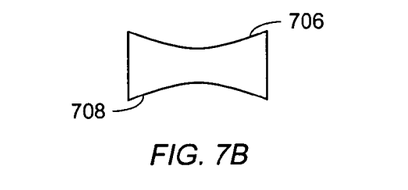
Figure 7C:
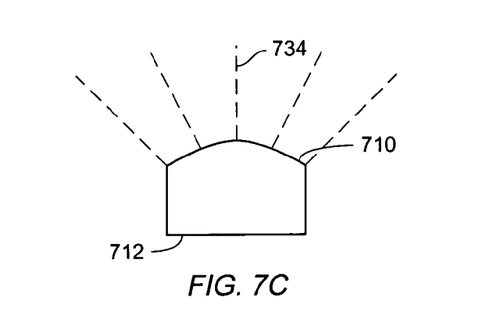
Figure 7D:
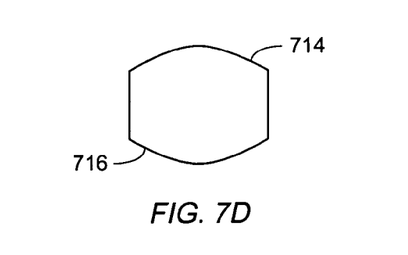
Figure 7E:
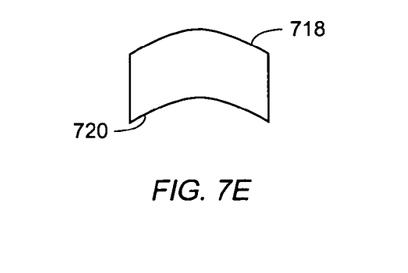

In addition, because multi-directional transducers allow for treatment in two or more directions, rotational interstitial probe arrangements, such as those depicted in FIGS. 5, 6A and 6B, may be configured to be smaller, e.g., having a reduced diameter, than conventional rotating interstitial probe arrangements. Further, because no acoustic isolation is required on any firing face, exemplary rotating interstitial probe arrangements can be made more compactly. For example, conventional arrangements have diameters ranging from approximately 5 mm to 30 mm or more. An exemplary multi-directional transducer arrangement as disclosed herein may have a diameter anywhere from approximately 1.5 mm to 100 mm or more.

A multi-directional transducer may be configured to provide radiation energy in various manners. For example, a multi-directional transducer can provide radiation in a substantially uniform manner, in a focused manner and/or in a defocused manner. Such configurations can include the shaping of the transduction element, e.g., the piezoelectric material, to provide energy as exemplified in FIGS. 7A-7E, the use of lenses to provide energy as exemplified in FIGS. 8A-8F, and/or electronic focusing to provide energy as exemplified in FIG. 9.

Figure 8A:
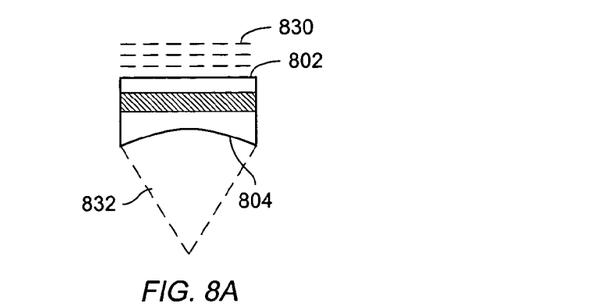
FIGS. 8A-8F illustrate exemplary embodiments of different lens curvatures for a transducer in accordance with the present invention.
Figure 8B:
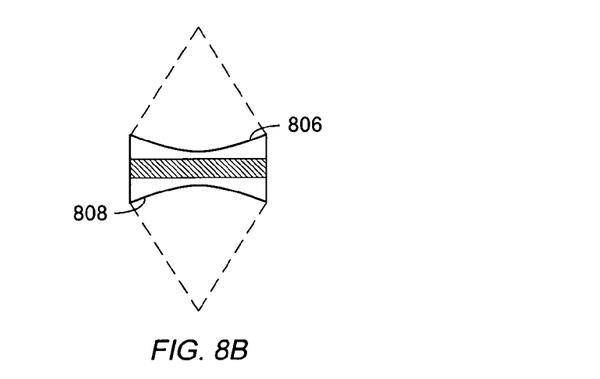
Figure 8C:
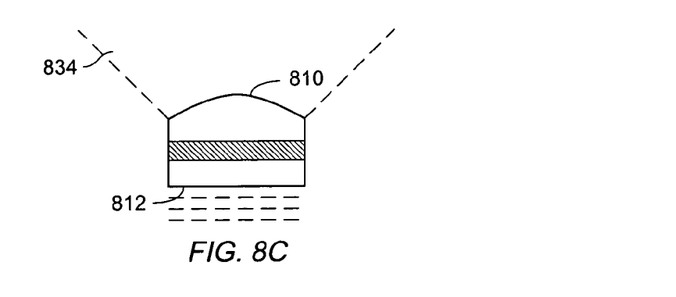
Figure 8D:
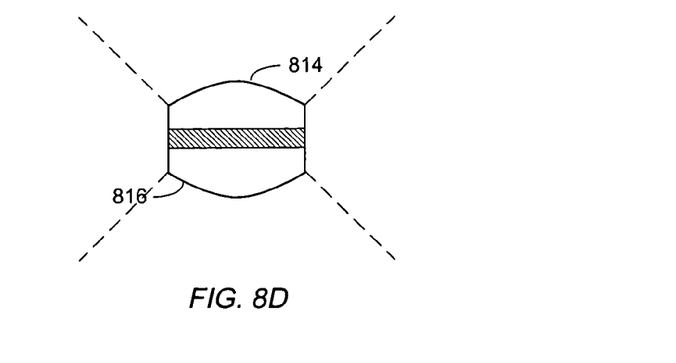
Figure 8E:
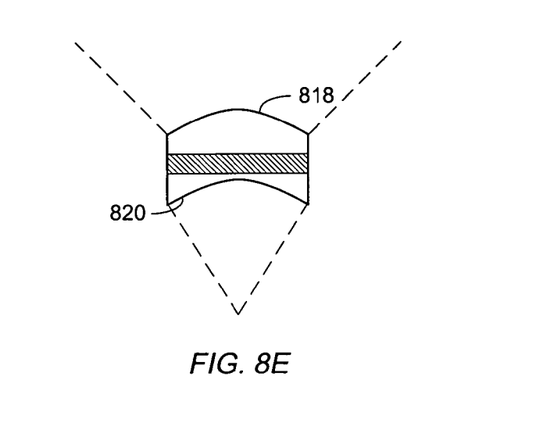
Figure 8F:
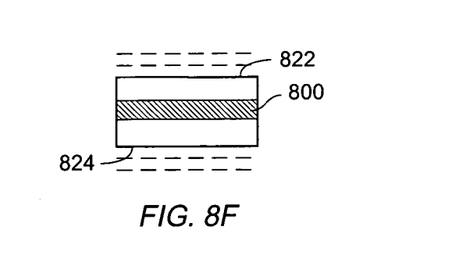

A substantially flat transduction element can radiate energy in a substantially uniform direction. For a flat transduction element that generates a plane wave pattern, the width of the element is larger as compared to that for a focused pattern. For example as illustrated in FIG. 4A, faces 406 and 408 can be configured substantially flat to radiate energy in a substantially uniform direction, i.e., to radiate approximately directly outwards from faces 406 and 408. In addition to having a flat surface for faces 406 and 408, a transduction element can be configured with a substantially flat lens to also radiate energy in a substantially uniform direction. An exemplary lens may comprise air, water, or other liquids and/or any other refractive material that can be utilized with transducers to provide a lens function. With reference to FIG. 8F, a substantially flat transduction element 800 can be coupled to a substantially flat lens 822 on a first side and a substantially flat lens 824 on a second side. The configuration depicted in FIG. 8F allows for energy to radiate in a substantially uniform direction from both lenses 822 and 824.

Figure 9:
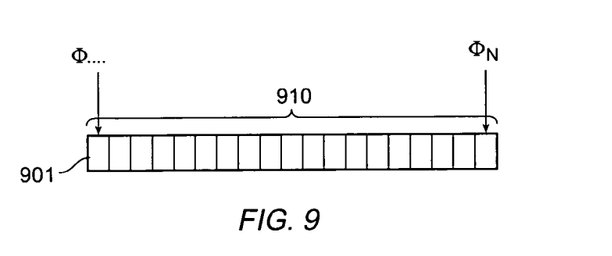
FIG. 9 illustrates an exemplary embodiment of another type of focusing for a transducer in accordance with the present invention.

Electronic focusing may also be used to radiate energy in a substantially uniform direction. As illustrated in FIG. 9, electronic focusing includes a phased array 910 of sectioned sub-apertures 901-909, each having an associated focusing value and translation value. Sub-apertures 901-909 comprise sections of a transduction element that can be suitably fired in a manner to provide a substantially uniform pattern. For example, sub-aperture 901 may be configured to have a focusing value of approximately zero and a translation value of approximately zero, thus allowing for energy to radiate in a substantially uniform direction. In other words, a zero focusing value corresponds to an absence of curvature of a sub-aperture, and a translation of zero equates to the direction and distance a sub-aperture can move. Adjustment of the relative delays to sub-apertures 901-909 can result in a phased array 910 becoming focused, defocused (creating a diverging wave), unfocused, and/or a combination of such effects.

A transduction element having a face configured in a concave manner can radiate energy in a focused or concentrated pattern. A concave configuration can cause energy to converge, and thus provide a focused pattern. For example, with reference to FIG. 7B, faces 706 and 708 can be curved in a concave manner to radiate energy in focused pattern. Faces 706 and 708 can be configured with a concave arrangement having any negative radius of curvature, or any other negative arc. In addition, a substantially flat transduction element can comprise a face coupled with a lens curved in a concave manner to radiate energy in a focused or concentrated pattern. The lens may comprise air, water, and/or any other refractive material, and have any negative radius of curvature. For example, with reference to FIG. 8B, a substantially flat transduction element 800 can be coupled to a concave lens 806 on a first side and a concave lens 808 on a second side, thus allowing for energy to radiate in a focused direction from both lenses 806 and 808. Moreover, electronic focusing may also be used to radiate energy in a focused manner. As illustrated in FIG. 9, sub-aperture 903 may be configured to have a focusing value of −1 and a translation value of zero, wherein the negative focusing value corresponds to concave curvature of sub-aperture 903, and the translation value of zero equates to the direction and distance a sub-aperture will move.

A transduction element having a face configured in a convex manner can radiate energy in a defocused or diffused pattern. A convex configuration can cause energy to diverge, and thus provide a defocused pattern. For example, with reference to FIG. 7D, faces 714 and 716 are configured in a convex manner to radiate energy in defocused manners. Faces 714 and 716 can be configured with a convex arrangement having any positive radius of curvature, or any other positive arc. In addition, a substantially flat transduction element having a face coupled with a lens curved in a convex manner can radiate energy in a defocused or diffused manner. A convex lens may comprise air, water, and/or any other refractive material, with any positive radius of curvature. For example, with reference to FIG. 8D, a substantially flat transduction element 800 can be configured with a convex lens 814 on a first side and a convex lens 816 on a second side, thus allowing for energy to radiate in a defocused direction from both lenses 814 and 816. Further, electronic focusing may also be used to radiate energy in a defocused manner. For example with reference again to FIG. 9, sub-aperture 905 may be configured to have a focusing value of 1 and a translation value of 0, wherein a positive focusing value corresponds to convex curvature of sub-aperture 905, and a translation value of zero equates to the direction and distance a sub-aperture will move. Accordingly, sub-aperture 905 can facilitate the transduction element to radiate energy in a defocused manner.

The above exemplary embodiments of multi-directional transducers configured for radiating in a substantially uniform, focused or defocused manner may also be suitably configured to provide any combination of substantially uniform, focused and/or defocused manners. For example, with reference to FIG. 7A, a transduction element can be configured to radiate energy in a substantially uniform manner 730 from a first substantially flat face 702 and radiate energy in a focused manner 732 from a face configured in a concave manner 704. In addition, with reference to FIG. 7C, a transduction element can be configured to radiate energy in a defocused manner 734 from a first convex face 710 and radiate energy in a uniform manner from a second substantially flat face 712. Similarly, with reference to FIG. 7E, a transduction element can be configured to radiate energy in a defocused manner from a first convex face 718 and radiate energy in a focused manner from a second concave face 720. While FIGS. 7A through 7E illustrate various curvatures of the faces of a transduction element, any of the faces of the transduction element may be curved or substantially flat in any combination to provide for radiation in a focused, defocused, and/or substantially uniform manner, and such faces are not limited to the embodiments illustrated.

Similarly, radiation patterns facilitated with use of a lens may also be configured for any combination of focusing, defocusing and/or uniform radiation. With reference to FIG. 8A, a transduction element 800 can radiate energy in a substantially uniform manner 830 from a first substantially flat lens 802 and can radiate energy in a focused manner 832 from a concave lens 804. In addition, with reference to FIG. 8C, transduction element 800 can radiate energy in a defocused manner 834 from a first convex lens 810 and radiate energy in a uniform manner from a substantially flat lens 812. Similarly, with reference to FIG. 8E, transduction element 800 can radiate energy in defocused manner from a convex lens 818 and radiate energy in a focused manner from a concave lens 820. While FIGS. 8A through 8F illustrate various lenses coupled with transduction element 800, any type of lens may be coupled to any side of transduction element 800 to provide for radiation in a focused, defocused, and/or substantially uniform manner, and such lenses are not limited to the embodiments illustrated.

Variations in multi-directional radiation may also be accomplished through various combinations of electronic focusing. For example, with reference to FIG. 9, sub-apertures 901, 903, 905, 907 and 909 may be configured to have any focusing value and any translation value to suitably allow for energy to radiate in any of a focused, defocused, and/or uniform manner.

Multi-directional transducers can also be configured with any combination of mechanisms for uniform, focused and/or defocused radiation patterns. For example, rather than utilizing a single mechanism such as piezoelectric focusing, with reference to FIGS. 7A-7E; lens focusing, with reference to FIGS. 8A-8F, or electronic focusing, with reference to FIG. 9, multi-directional radiation may also be configured through any combination of mechanisms for piezoelectric focusing, lens focusing, and/or electronic focusing radiation patterns, and such multi-directional radiation is not limited to the embodiments illustrated. For example, a transduction element can be configured with a first concave face for radiating energy in a focused manner, and a second substantially flat face configured with a convex lens for radiating energy in a defocused manner, or with electronic focusing to provide a defocused pattern. Accordingly, multi-directional transducers can be configured in any manner to provide uniform, focused and/or defocused radiation patterns.

While exemplary embodiments of a multi-directional transducer have provided for a single transduction element, such as that illustrated with reference to FIG. 4A, a multi-directional transducer may be configured to use multiple elements and/or as a multiple-element array.

Figure 10:
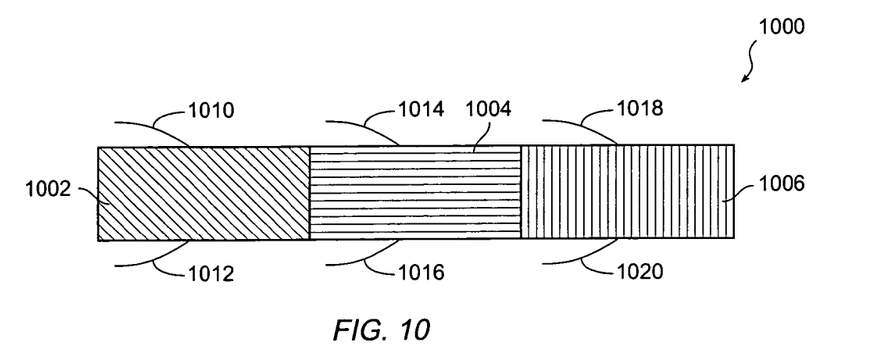
FIG. 10 illustrates an exemplary embodiment of a multi-element, multi-directional transducer in accordance with the present invention.

For example, with reference to FIG. 10, a multi-directional transducer 1000 may comprise multiple transduction elements, such as a transduction element 1002, a transduction element 1004, and a transduction element 1006. While three transduction elements 1002, 1004, and 1006 are depicted in FIG. 10, multi-directional transducer 1000 may also comprise two, four, or more transduction elements. In addition, transduction elements 1002, 1004, and 1006 may comprise any transduction element configured for radiating energy in two or more directions. Further, transduction elements 1002, 1004, and 1006 may be coupled to electronic leads 1010 and mechanically mounted in any manner. For example, transduction elements 1002, 1004 and/or 1006 can be configured to fire individually, or simultaneously with or without common lead connections.

Figure 11:
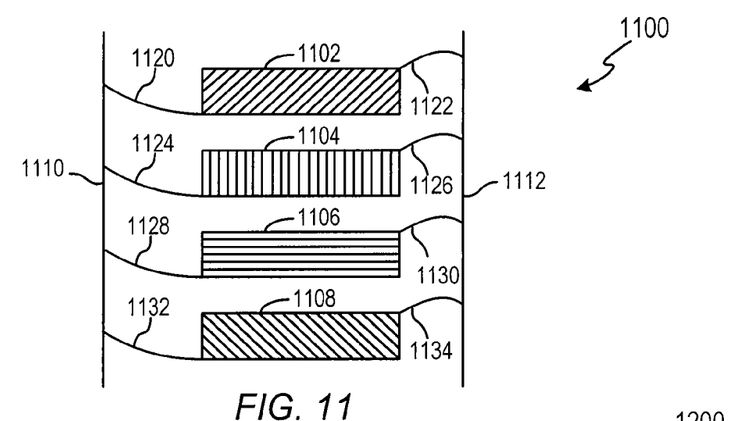
FIG. 11 illustrates an exemplary embodiment of a multi-element array of multi-directional transducers in accordance with the present invention.

In addition, with reference to FIG. 11, a multi-directional transducer 1100 may comprise two or more transduction elements 1102, 1104, 1106 and 1108 configured as an array. While four transduction elements 1102, 1104, 1106 and 1108 are illustrated in FIG. 11, multi-directional transducer 1100 may comprise an array with two, three, five, or more transduction elements. In addition, transduction elements 1102, 1104, 1106 and 1108 may comprise any transduction element configured for radiating energy in two or more directions. Further, transduction elements 1102, 1104, 1106 and 1108 may be coupled to electronic leads 1010 and mechanically mounted in any manner. For example, transduction elements 1102, 1104, 1106 and 1108 may be coupled through corresponding electronic leads 1120-1134 to common electrical leads 1110 and 1112. Other variations can be suitably implemented.

Further, in addition to the side-by-side arrangement illustrated in multi-directional transducer 1000, and the parallel arrangement illustrated in multi-directional transducer array 1100, an exemplary multi-directional transducer can also be configured in a stacked configuration. For example, with reference to FIG. 12, a stacked multi-directional transducer 1200 can comprise a first transduction element 1202A having a first electrode lead 1214A and a second electrode lead 1214B defined via the direction of electromechanical transduction activity, or piezoelectric poling, and a second transduction element 1202B, having a first electrode lead 1216A and second electrode lead 1216B, likewise defined via the direction of electromechanical transduction activity, or piezoelectric poling. Transduction elements 1202A and 1202B have respectively a first firing face 1206 and a second firing face 1208 configured to provide ultrasound radiation in two or more directions 1210 and 1212. Transduction elements 1202A and 1202B can be suitably joined via a layer or multiple layers 1204. Transduction elements 1202A and 1202B radiate acoustical energy from faces 1206 and 1208 in a manner depending on various characteristics, including the material composition and configuration of 1202A and 1202B, the layer or multiple layers 1204, any acoustic loading in the directed areas 1210 and 1212, and/or the electronic drive and connections at electrodes 1214A, 1214B, 1216A and 1216B. Accordingly, by suitably changing one or more characteristics of transduction elements 1202A and 1202B, a very wide set of acoustic responses may be implemented.

Figure 12:
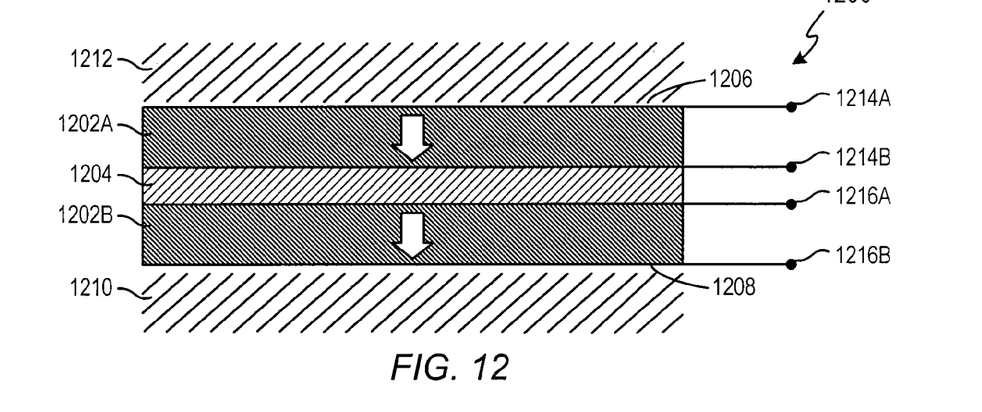
FIG. 12 illustrates another exemplary embodiment of a multi-element, multi-directional transducers in accordance with the present invention.

For example, a single layer or multiple layer 1204 can be made acoustically comparable to a wavelength of interest, and/or adjustable in thickness. In such instances, the resonant character of a stacked multidirectional transducer can be suitably modified and tunable to different properties.

As another example, if transduction elements 1202A and 1202B comprise substantially the same structure and are electromechanically oriented along the same direction, and in addition layer 1204 is acoustically thin, then acoustical or sound radiation from firing faces 1206 and 1208 will be determined in part by the electronic drive at connections to electrodes 1214A, 1214B, 1216A and 1216B. In the event electrodes 1214B and 1216A are electrically shorted together, and electrodes 1214A and 1216B are driven, a series connection results. In such a case the effective thickness of stacked multidirectional transducer 1200 is approximately twice as large as that of a transducer comprising a single transduction element 1202A or 1202B, and thus the resonance frequency is halved. Moreover, since stacked multidirectional transducer 1200 includes an odd harmonic resonance, another resonance exists at approximately three times the fundamental resonance.

In another example, if transduction elements 1202A and 1202B comprise substantially the same structure and are electromechanically oriented along the same direction, and in addition layer 1204 is acoustically thin, then if electrodes 1214B and 1216A are electrically shorted together, and electrodes 1214A and 1216B are electrically shorted together, and the pair of shorted connections are driven, a parallel connection results. In such a case the effective particle displacement of stacked multidirectional transducer 1200 is approximately twice as large as that of a single transduction element 1202A or 1202B, and thus the power output is approximately quadrupled while the resonance frequency stays the same. Further, if the transduction element has a fundamental resonance at $f_0$, by electronically or manually switching electrodes 1214A, 1214B, 1216A, and 1216B to achieve a series connection or parallel connection, access to resonance frequencies $f_0/2$, $f_0$, and $3f_0/2$ can be realized.

In any of the exemplary embodiments, one of transduction elements 1202A and 1202B can be used for one function, such as imaging, therapy or tissue parameter monitoring, and the other transduction element can be utilized for the same or different function. Moreover, the acoustic loading of the stacked configuration of transduction elements 1202A and 1202B can be suitably changed to vary the frequency response of stacked multi-directional transducer 1200.

Additional changes to the structure of transduction elements 1202A and 1202B, e.g., sizes, shapes, orientations and the like, and/or to the acoustical loading can also facilitate a wide set of acoustic responses, alone or in combination with the other changes to the electrodes or layers. Accordingly, stacked multidirectional transducer 1200 can be suitably modified in various manners to provide a wide set of acoustic responses.

Figure 13:
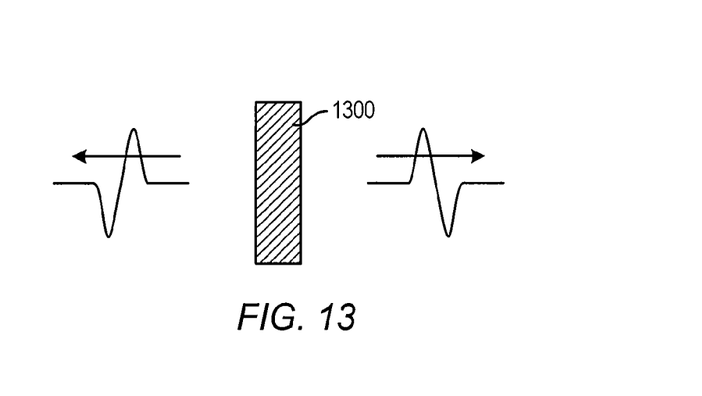
FIG. 13 illustrates an exemplary embodiment for pulse-echo imaging in accordance with the present invention.

In accordance with an exemplary embodiment, a multidirectional transducer may be utilized for various imaging applications. For example, with reference to FIG. 13, a multi-direction transducer may utilize pulse-echo imaging techniques wherein a resulting image can be provided by a combination of images at one or more faces of a transduction element 1300, i.e., a summed or combined image may be formed from acoustical energy received from two or more direction. In accordance with another exemplary embodiment, to facilitate imaging in only a single direction, an acoustical damper, absorber or mask may be interposed at various spatial positions to suitably block, reflect, and/or absorb ultrasound energy, i.e., the acoustical damper, absorber or mask can be suitably inserted into the path(s) of one or more faces of transduction element 1300 such that any returned echoes originate from a single region of interest. In addition to this exemplary technique, any other pulse-echo imaging technique now known or hereinafter devised can also be suitably implemented with an exemplary multi-directional transducer.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultrasound therapy with a multi-directional transducer is described above is suitably for use by a medical practitioner proximate the patient, the system can also be accessed remotely, i.e., the medical practitioner can view through a remote display having imaging information transmitted in various manners of communication, such as by satellite/wireless or by wired connections such as IP or digital cable networks and the like, and can direct a local practitioner as to the suitably placement for the transducer. These and other changes or modifications are intended to be included within the scope of the present invention, as set forth in the following claims.

We claim:

1. An ultrasound system for facilitating treatment to at least two regions of interest, said ultrasound system comprising:
    a control system configured to control operation of said ultrasound system; and
    a multi-directional transducer configured for facilitating treatment in the at least two regions of interest, said multi-directional transducer comprising a single first transduction element, said single first transduction element having both a first firing face adjacent to and facing a first region of interest that is configured for radiating ultrasound energy to provide a first radiation pattern from said first firing face and a second firing face adjacent to and facing a second region of interest that is configured for radiating a second radiation pattern from said second firing face, wherein said second radiation pattern is different from said first radiation pattern and wherein said both first radiation pattern and said second radiation pattern are emitted on a single emission axis that is parallel to an axis of electrical excitation within said single first transduction element and wherein said single first transduction element expands and contracts in the same direction as said axis of electrical excitation and does not substantially expand and contract in a direction that is not parallel to the axis of electrical excitation.

2. An ultrasound system according to claim 1, wherein said single first transduction element comprises a single piezoelectrically active material.

3. An ultrasound system according to claim 2, wherein said piezoelectrically active material comprises at least one of lead zirconante titanate, lead titanate, barium titanate, lead metaniobate and lithium niobate.

4. An ultrasound system according to claim 2, wherein said single first transduction element further comprises a matching layer configured along said piezoelectrically active material.

5. An ultrasound system according to claim 1, wherein said multi-directional transducer comprises:
    an electrical coupling for enabling transfer of signals to and from said single first transduction element;
    a mechanical mounting mechanism configured to reduce interference from said electrical coupling; and
    wherein said single first transduction element has a width at least two times the size of said single first transduction element's thickness.

6. An ultrasound system according to claim 1, wherein said second firing face is configured to provide damping effects to acoustical energy provided by said first firing face.

7. An ultrasound system according to claim 1, wherein said second firing face is configured without acoustic isolation.

8. An ultrasound system according to claim 7, wherein said first firing face and said second firing face are configured with acoustical loading.

9. An ultrasound system according to claim 1, wherein said first firing face and said second firing face are substantially opposed.

10. An ultrasound system according to claim 1, wherein said first firing face and said second firing face are configured to generate ultrasound energy simultaneously in at least two directions.

11. An ultrasound system according to claim 1, wherein said first firing face and said second firing face are configured to generate ultrasound energy in an alternating manner in at least two directions.

12. An ultrasound system according to claim 1, wherein said ultrasound system further comprises a tubular member configured for covering said multidirectional transducer to facilitate invasive treatment.

13. An ultrasound system according to claim 12, wherein said multidirectional transducer is configured for at least one of rotational and translational movement.

14. An ultrasound system according to claim 1, wherein said control system is configured for capturing two-directional information from said multi-directional transducer with respect to a patient, and to assess the information to facilitate multi-directional therapy.

15. An ultrasound system according to claim 1, wherein said single first transduction element comprises more than two firing faces configured for radiating ultrasound energy to provide more than two radiation patterns.

16. An ultrasound system according to claim 1, wherein said multi-directional transducer comprises a combined ultrasonic imaging, therapy and temperature monitoring transducer.

17. An ultrasound system according to claim 1, wherein said ultrasound system further comprises a coupling system configured for acoustic coupling between said multi-directional transducer and the at least two regions of interest.

18. An ultrasound system according to claim 17, wherein said coupling system is configured for controlled cooling of an interface surface proximate to the at least two regions of interest to facilitate control of thermal energy effects of said ultrasound system.

19. The ultrasound system according to claim 1, wherein said multi-directional transducer is a hand-held multi-directional transducer probe.

20. The ultrasound system according to claim 1, wherein said first radiation pattern and said second radiation pattern are the only two patterns of energy emission.

21. A multidirectional transducer configured for facilitating treatment to at least two regions of interest, said multidirectional transducer comprising:
a hand-held probe;
a single first transduction element disposed within said hand-held probe, said single first transduction element having both a first firing face adjacent to and facing a first region of interest configured for radiating ultrasound energy in a first radiation pattern from said first firing face; and a second firing face adjacent to and facing a second region of interest configured for radiating ultrasound energy in a second radiation pattern from said second firing face; wherein both said first radiation pattern and said second radiation pattern are emitted on a single emission axis wherein said single first transduction element expands and contracts in the same direction as an axis of electrical excitation within said single first transduction element and does not substantially expand and contract in a direction that is not parallel to the axis of electrical excitation.

22. A multidirectional transducer according to claim 21, wherein said single first transduction element comprises a single piezoelectrically active material comprising at least one of lead zirconante titanate, lead titanate, barium titanate, lead metaniobate and lithium niobate.

23. A multidirectional transducer according to claim 22, wherein said single first transduction element further comprises a matching layer configured along said piezoelectrically active material.

24. A multidirectional transducer according to claim 21, wherein said single first transduction element comprises a mechanical mounting mechanism configured to reduce interference from electrical connections coupled to said single first transduction element.

25. A multidirectional transducer according to claim 24, wherein said first firing face and said second firing face are configured to generate ultrasound energy simultaneously in at least two directions.

26. A multidirectional transducer according to claim 21, wherein said second firing face is configured to provide damping effects to acoustical energy provided by said first firing face, and said first firing face and said second firing face are configured with acoustical loading.

27. A multidirectional transducer according to claim 21, wherein said first firing face and said second firing face are substantially opposed.

28. A multidirectional transducer according to claim 27, wherein said first firing face and said second firing face are configured to generate ultrasound energy in an alternating manner in at least two directions.

29. A multidirectional transducer according to claim 21, wherein said single first transduction element comprises more than two firing faces configured for radiating ultrasound energy to provide more than two radiation patterns.

30. A multidirectional transducer according to claim 21, wherein each of said first firing face and said second firing face are configured with one of a flat, concave, and convex surface.

31. A multidirectional transducer according to claim 30, wherein said first firing face and said second firing face are configured with different surfaces.

32. A multidirectional transducer according to claim 21, wherein each of said first firing face and said second firing face are configured with a flat surface and respectively coupled to a first lens and a second lens.

33. A multidirectional transducer according to claim 32, wherein each of said first lens and said second lens are configured with one of a flat, concave, and convex surface.

34. A multidirectional transducer according to claim 33, wherein said first lens and said second lens are configured with different surfaces.

35. A multidirectional transducer according to claim 21, wherein said multi-directional transducer comprises a phased array configured for electronic focusing.

36. The multi-directional transducer according to claim 21, wherein said hand-held probe is a rigid member configured to be used to treat a patient non-invasively.

37. The multi-directional transducer according to claim 21, wherein said single first transduction element has a width approximately two times the size of said single first transduction element's thickness.

38. A method for multi-directional ultrasound treatment comprising:
generating radiation energy in a multi-directional transducer substantially in only two directions along a single emission axis that is parallel with an axis of electrical excitation of said multi-directional transducer;
radiating acoustical energy having a first radiation pattern from a first firing face of a single first transduction element of said multi-directional transducer to provide treatment in a first direction for facilitating treatment in a first region of interest; and
radiating acoustical energy having a second radiation pattern from a second firing face of said single first transduction element of said multi-directional transducer to provide treatment in a second direction for facilitating treatment in a second region of interest, wherein said first radiation pattern is different from said second radiation pattern.

39. The method according to claim 38, wherein said radiating of acoustical energy occurs from at least one of a flat, concave, and convex surface of said first firing face and said second firing face.

40. The method according to claim 38, wherein said radiating of acoustical energy occurs simultaneously from said first firing face and said second firing face.

41. The method according to claim 38, wherein said multi-directional transducer is a rigid, hand-held probe.

42. The method according to claim 41, further comprising the step of moving said multi-directional, rigid, hand-held probe across an external surface of a patient's body.

43. An ultrasound system for facilitating treatment to at least two regions of interest, said ultrasound system comprising:

a control system configured to control operation of said ultrasound system; and a multi-directional transducer configured for facilitating treatment in the at least two regions of interest, said multi-directional transducer comprising a single first transduction element, said single first transduction element having both a first firing face adjacent to and facing a first region of interest that is configured for radiating ultrasound energy to provide a first radiation pattern from said first firing face and a second firing face adjacent to and facing a second region of interest that is configured for radiating a second radiation pattern from said second firing face, and wherein said both first radiation pattern and said second radiation pattern are emitted on a single emission axis that is parallel to an axis of electrical excitation within said single first transduction element and wherein said single first transduction element expands and contracts in the same direction as said axis of electrical excitation and does not substantially expand and contract in a direction that is not parallel to the axis of electrical excitation.

44. The ultrasound system according to claim 43, wherein the first radiation pattern and the second radiation pattern are the same.

45. The ultrasound system according to claim 43, wherein the first radiation pattern and the second radiation pattern are different.

* * * * *